United States Patent [19]
Steinberg et al.

[11] Patent Number: 5,914,235
[45] Date of Patent: Jun. 22, 1999

[54] POTENTIATION OF [³H] 2-(2-BENZOFURANYL)-2-IMIDAZOLINE (BFI) BINDING SITES IN HUMAN TISSUE BY TRANYLCYPROMINE (TCP)

[75] Inventors: Mitchell Irvin Steinberg; Sally Ann Wiest, both of Indianapolis, Ind.

[73] Assignee: Eli Lilly and Company, Indianapolis, Ind.

[21] Appl. No.: 08/936,929

[22] Filed: Sep. 25, 1997

Related U.S. Application Data

[60] Provisional application No. 60/028,333, Oct. 11, 1996.
[51] Int. Cl.⁶ ................................................. G01N 33/567
[52] U.S. Cl. .............................. 435/7.1; 435/4; 435/7.21; 435/7.93; 435/25
[58] Field of Search ................................ 435/4, 7.1, 7.21, 435/7.93, 25

[56] References Cited

PUBLICATIONS

P. Bousquet, et al. "Role of the Ventral Surface of the Brain Stem in the Hypotensive Action of Clondine." *European Journal of Pharmacology* 34:151–156 (1975).
F. Tesson and A. Parini. "Identification of an imidazoline–guanidinium receptive site in mitochondria from rabbit cerebral cortex." *European Journal of Pharmacology* 208:81–83 (1991).
F. Tesson, et al. "Tissue-specific localization of mitochondria imidazoline–guanidinium receptive sites." *European Journal of Pharmacology* 219:335–338 (1992).
C. Carpene, et al. "Inhibition of Amine Oxidase Activity by Derivatives that Recognize Imidazoline I2 Sites." *The Journal of Pharmacology and Experimental Therapeutics* 272(2):681–688 (1995).
S. Wiest and M. Steinberg. "Binding of [³H] 2–(2–benzofuranyl) –2–imidazoline (BFI) to human brain: Potentiation by Tranylcypromine." *Life Sciences* 60(9):605–615 (1997).
D. J. Nutt, et al. "Functional Studies of Specific Imidazoline–2 Receptor Ligands." *Annals New York Academy of Sciences* 763:125–139 (1995).
C. M. Brown, et al. "RS–45041–190: a selective, high–affinity ligand for I₂ imidazoline receptors." *British Journal of Pharmacology* 116:1737–1744 (1995).
M. Pigini, et al. "Imidazoline Receptors: Qualitative Structure–Activity Relationships and Discovery of Tracizoline and Benazoline. Two Ligands with High Affinity and Unprecedented Selectivity." *Bioorganic and Medicinal Chemistry* 5(5):833–841 (1997).
Alemany, et al. "LSL 60101, a selective ligand for imidazoline I₂ receptors, on glial fibrillary acidic protein concentration." *European Journal of Pharmacology* 280:205–210 (1995).

*Primary Examiner*—Ponnathapura Achutamurthy
*Attorney, Agent, or Firm*—Thomas D. Webster

[57] ABSTRACT

The present invention relates to a process for discovering compounds that modulate novel I₂ binding sites (e.g. BFI binding sites) in human tissue, as well as a process for identifying TCP-like compounds that potentiate BFI binding.

4 Claims, 7 Drawing Sheets

POTENTIATION OF [³H] 2-(2-BENZOFURANYL)-2-IMIDAZOLINE (BFI) BINDING SITES IN HUMAN TISSUE BY TRANYLCYPROMINE (TCP)

This application claims benefit of Provisional Application 60/028,333 filed Oct. 11, 1996.

FIELD OF THE INVENTION

The present invention relates to a process for discovering compounds that modulate novel BFI binding sites in human tissue, as well as to a process for identifying TCP-like compounds that potentiate BFI Binding.

BACKGROUND OF THE INVENTION

Imidazoline receptors were first proposed based on the observation that the vasodepressor action of centrally administered clonidine could not be mimicked or blocked by adrenergic compounds lacking an imidazoline structure [P. Bousquet, et al., Eur. J. Pharmacol. 34:151–156 (1975)]. Later, radioligand binding studies in bovine ventrolateral medulla using labelled clonidine and idazoxan demonstrated two populations of nonadrenergic binding sites, now referred to as imidazoline binding sites $I_1$ (labeled by clonidine) and $I_2$ (labeled by idazoxan) [P. Ernsberger, et al., Eur. J. Pharmacol. 134:1–13 (1987)].

$I_1$-sites are localized to plasma membranes, enriched in ventrolateral medullary neurons, kidney medulla and platelets and appear functionally coupled to central sympathetic outflow. $I_2$-sites also are widely distributed throughout the mammalian brain and periphery (liver, kidney cortex, fat cells, platelets, placenta, vascular smooth muscle and endothelium) [S. Regunathan, et al, J. Pharmacol. Exp. Ther. 276:1272–1282 (1996); M. C. Michel, et al, TIPS 10:342–344 (1989) and S. Regunathan, et al, Ann. Rev. Pharmacol. Toxicol. 36:511–544 (1996)], but their functional role is uncertain. [D. J. Nutt, et al, *The imidazoline receptor: pharmacology, functions, ligands, and relevance to biology and medicine*, D. J. Reis, P Bousquet and A. Parini (Eds.) 125–139, The New York Acadamy of Sciences, New York (1995)].

Monoamine oxidase (MAO) activity is closely coupled with $I_2$ binding [F. Tesson, et al., Eur. J. Pharmacol. 208:81–83 (1991)]. Both [³H]idazoxan binding and enzymatic activity are co-localized to the mitochondrial outer membrane [F. Tesson, et al., J. Biol. Chem., 279:9856–9861 (1995)]. Partially purified $I_2$ binding protein has been shown to possess amino acid sequences in common with MAO-A and MAO-B. Yeast cells transformed with recombinant cDNA encoding human MAO-A or MAO-B, express a protein that specifically binds [³H]idazoxan [F. Tesson, et al., J. Biol. Chem. 270:9856–9861 (1995)]. It appears, however, that the substrate (or active) binding site of the enzyme is distinct from the $I_2$ ligand recognition site [I. Limon-Boulez, et al., J. Pharmacol. Exp. Ther. 276:359–364 (1996); C. Carpene et al, J. Pharmacol. Exp. Ther. 272:681–688 (1995); and R. Raddatz, et al., J. Biol. Chem. 270:27961–27968 (1995)].

Also, a disparity in MAO activity and imidazoline binding has been seen using the irreversible $I_2$ binding ligand (¹²⁵I)AZIPI such that photolabeling could be demonstrated in liver membranes but not in platelets despite equivalent amount of MAO B activity. [R. Raddatz, et al, J. Biol. Chem., 270:27961–8 (1995)].

MAO activity is widely distributed, but the expression of $I_2$ sites appears to be tissue specific [F. Tesson, et al., Eur. J. Pharmacol. 219:335–338 (1992)]. Thus, it remains conjectural whether $I_2$ sites and MAO are the same protein in all tissues [S. Regunathan, et al, Ann. Rev. Pharmacol. Toxicol. 36:511–544 (1996)].

Binding to $I_2$-sites was initially described using the non-selective $\alpha_2$ antagonist [³H]idazoxan in the presence of an $\alpha_2$-receptor mask [M. C. Michel, et al, TIPS 10:342–344 (1989)]. Recently, highly selective $I_2$-ligands have been described such as 2-(3-azido or amino-4-iodophenoxyl) methyl imidazoline [S. M. Lanier, et al., J. Biochem. Mol. Biol. 268:16047–16051 (1993)); B. Ivkovic, et al., Mol. Pharmacol. 46:15–23 (1994)), and 2-(2-benzofuranyl)-2-imidazoline (BFI) [D. J. Nutt, et al., *The imidazoline receptor: pharmacology, functions, ligands, and relevance to biology and medicine,* D. J. Reis, et al., (Eds.) 125–139, The New York Academy of Sciences, New York (1995) (Eds.)]. Unlabelled BFI is over 20 times more selective for [³H]idazoxan sites in rat liver ($I_2$) compared to [³H]RX821002 sites in hamster adipocytes) [C. Carpene, et al., J. Pharmacol. Exp. Ther. 272:681–688 (1995)]. Further, in rabbit whole brain membranes, [³H]BFI binds with high affinity to an apparent single population of sites and has nearly 3 orders of magnitude greater selectivity for $I_2$ sites than for $\alpha_2$ sites [D. J. Nutt, et al., *The imidazoline receptor: pharmacology, functions, ligands, and relevance to biology and medicine,* D. J. Reis Bousquet, P. and Parini, A., 125–139, The New York Academy of Sciences, New York (1995)]. As yet, there is no information available on the relationship between [³H]BFI binding and MAO activity in human tissues.

Tranylcypromine (TCP) is a non-selective cyclopropylamine MAO inhibitor, that acts as a highly effective antidepressant agent although its use is restricted because of potential side effects associated with its inhibitory action on MAO.

There exists a need to develop compounds which mimic the effects of TCP without the adverse side effects associated with TCP.

SUMMARY OF THE INVENTION

It has now been found that [³H]BFI binds to human tissue in a way that is dissimilar to previously known binding characteristics of previously known $I_2$ ligands such as [³H] idazoxan. Accordingly, it is now possible to utilize these newly discovered binding sites as an important target in assays for the development of new pharmaceutical compounds which can be used for the treatment of various disorders.

The present invention is directed to a process for developing pharmaceutical compounds for the treatment of various disorders associated with newly described binding sites of [³H]BFI and other selective $I_2$ binding ligands that are greatly increased in the presence of TCP. The present invention is directed to an assay for detecting modulators of the potentiated binding sites. The present invention is also directed to an assay for detecting TCP-like compounds which inhibit MAO to a lesser degree than TCP.

DETAILED DESCRIPTION OF THE INVENTION

As used herein, "selective $I_2$ ligand" means a compound that contains an imidazoline nucleus, such as BFI, BU224, BU239 (Nutt et.al. *New York Acad. Sci.* 763, 125, 1995), RS 45041–190 (Brown et.al. *Br.J.Pharmocol.* 116, 1737, 1995), Tracizoline, and Benazoline (Pigini et.al. *Bioorg. Med. Chem.* 5, 833, 1997).

Figure 1A:
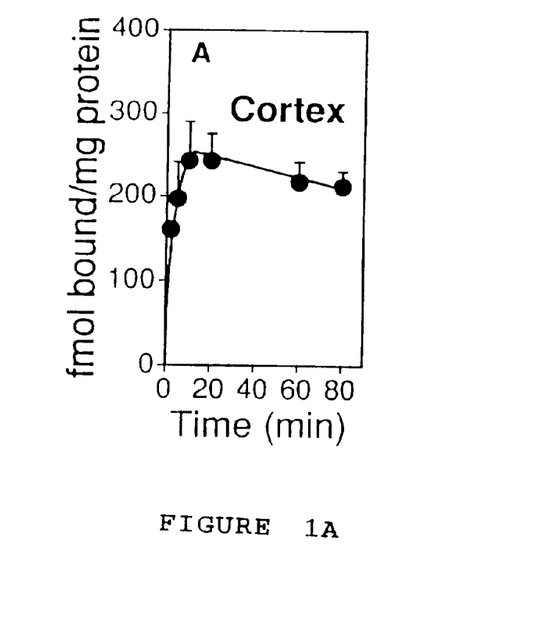
FIG. 1A depicts the time course for equilibrium of [³H] BFI binding in human cortex and FIG. 1B depicts saturation of [³H]BFI in human brain.
Figure 1B:
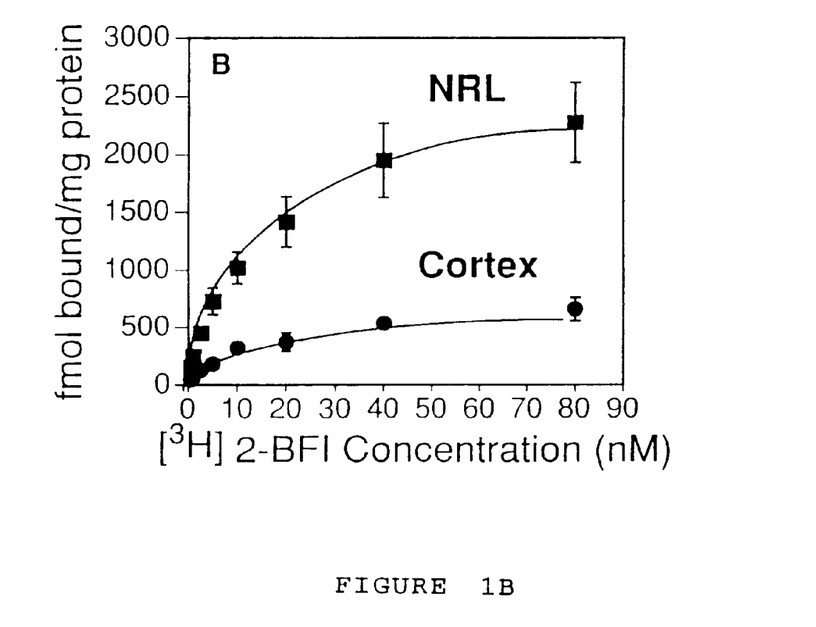

[$^3$H]BFI labels a binding site in human brain that appears similar to $I_2$ sites previously described using [$^3$H]BFI in rabbit brain. As shown in FIG. 1, [$^3$H]BFI binds to human cortex with high affinity (11.9 nM) to an apparent single population of sites ($B_{max}$=471 fmol/mg) similar to previously reported binding constants for [$^3$H]BFI in rabbit cortex ($K_D$=2.7 nM, $B_{max}$=451 fmol/mg). Furthermore, [$^3$H]BFI binding demonstrates a competitive displacement profile consistent with $I_2$ binding as defined using [$^3$H]idazoxan in human and rat brain [A. Miralles, et al., J. Pharmacol. Exp. Ther. 264:1187–1197 (1992)]. Thus, cirazoline (an imidazoline) and guanabenz (a guanidinium) competed for [$^3$H]BFI binding with high affinity whereas purported $I_1$-ligands (i.e., clonidine and moxonidine) and the selective imidazoline $\alpha_2$ antagonist, RX821002, competed with low affinity (see FIG. 2). In agreement with previously reported data in human brain using [$^3$H]idazoxan as an $I_2$ site ligand [H. Devos, et al., Neuroscience 59:589–598 (1994)], human NRL was found to have four times the number of [$^3$H]BFI sites found in cortex (see FIG. 1) thereby suggesting that idazoxan labels only $I_2$ sites in this study. Although not shown, amiloride possessed low affinity for the [$^3$H]BFI site, similar to findings using [$^3$H]idazoxan in human brain [A. Miralles, et al., J. Pharmacol. Exp. Ther. 264:1187–1197 (1992)] suggesting that [$^3$H]BFI is binding to the $I_{2b}$ subtype (P. R. Ernsberger, et al., J. Cardiovasc. Pharmacol. 20 (Suppl. 4) S1–S10 (1992)] as opposed to the $I_{2a}$ subtype that possesses high affinity for amiloride [C. Hamilton, et al., Pharmacol. 11:277–283 (1991)]. Together these results suggest that the [$^3$H]BFI binding site described herein in human brain is consistent with the proposed definition for an $I_2$ binding site [S. Regunathan, et al, Ann. Rev. Pharmacol. Toxicol. 36:511–544 (1996); A. Parini, Ann. NY Acad. Sci. 763:100–105 (1995)].

However, an important difference was noted in the binding pattern between BFI and idazoxan. Unlike [$^3$H]idazoxan, [$^3$H]BFI binding is markedly potentiated in the presence of low concentrations of TCP (see FIGS. 3A and 4B). The modification of [$^3$H]BFI binding by increasing concentrations of TCP is biphasic such that binding is potentiated maximally at 300 nM with reversal of potentiation between 300 nM and 10 $\mu$M and inhibition at concentrations >10 $\mu$M (see FIG. 3A). In experiments where membranes were pre-incubated with TCP and then washed to remove free TCP, [$^3$H]BFI binding was also biphasic with maximum potentiation seen at 1 $\mu$M (see FIG. 6). Thus, the binding potentiation is not dependent on free TCP (analogous to its MAO inhibitory activity, vide infra). Likewise, it is unlikely that the inhibitory phase of [$^3$H]BFI binding seen after maximal potentiation can be ascribed to simple competition for [$^3$H]BFI binding sites by high concentrations of free TCP. With the exception of slight potentiation by 1 $\mu$M phenelzine, other irreversible MAO inhibitors including clorgyline and pargyline did not potentiate binding (see FIG. 4c).

By virtue of its greater selectivity for $I_2$ sites versus $\alpha_2$ sites, we have demonstrated the utility of using [H]-BFI as a tool to uncover novel $I_2$ binding sites by TCP. Other selective $I_2$ ligands containing an imidazoline nucleus are also useful as a means to identify novel TCP binding sites. Examples of such ligands include BU224, BU239 (Nutt et.al. *New York Acad. Sci.* 763, 125, 1995), RS 45041–190 (Brown et.al. *Br.J.Pharmocol.* 116, 1737, 1995), Tracizoline, and Benazoline (Pigini et.al. *Bioorg. Med. Chem.* 5, 833, 1997).

The ability of TCP to potentiate the binding of [$^3$H]BFI and other imidizoline-containing compounds that act as $I_2$ specific ligands, provides a basis for developing agents which act to modulate the newly potentiated binding sites. It would be desirable, therefore, to identify those agents which bind the newly potentiated binding sites. Generally, such an assay includes a process for determining whether a substance is a functional ligand of the binding sites, said method comprising contacting a functional compound of the $I_2$ binding sites with said substance, monitoring binding activity by physically detectable means, and identifying those substances which effect a chosen response.

The instant invention provides such a screening system useful for discovering agents which compete with [$^3$H]BFI and related compounds for binding to the newly potentiated binding sites, said screening system comprising the steps of:

a) preparing tissue preps selected from human brain, kidney or platelets;

b) exposing said tissue preps to TCP and a test compound;

c) exposing the tissue preps to [$^3$H]BFI simultaneously with or following the introduction of the test compound;

d) removing non-specifically bound test compound and [$^3$H]BFI; and e) quantifying the concentration of bound test compound and/or [$^3$H]BFI.

The ensuing description and examples, while directed at BFI as an illustration, are not meant to be exclusive thereof. Other compounds, for example, BU224, BU239, RS45041–190, Tracizoline, and Benazoline are also contemplated. This process allows one to rapidly screen for compounds which modulate the newly potentiated [$^3$H]BFI/$I_2$ receptor complex. Utilization of the screening system described above provides a sensitive and rapid means to determine those compounds which interfere with the formation of the [$^3$H]BFI/$I_2$ receptor complex. This screening system may also be adapted to automated procedures such as a PANDEX® (Baxter-Dade Diagnostics) system allowing for efficient high-volume screening of potential therapeutic agents.

In such a screening protocol the tissue preps ($I_2$ receptor complex) is prepared as described in the Examples supra. In the alternative, the complex is prepared by known recombinant DNA technology techniques for synthesis of recombinant MAO proteins.

The receptor may be free in solution or bound to a membrane. Whether the receptor is bound to a membrane or is free in solution, it is generally important that the conformation of the protein be conserved. In a preferred practice of the invention, therefore, the receptor is suspended in a hydrophilic environment.

A sample of a test compound is then introduced to the reaction vessel containing the membrane protein (which is obtained from any human source) simultaneously with the addition of TCP. Alternatively, TCP may be added prior to the introduction of the test compound or following the introduction of the test compound. [$^3$H]BFI is then added to the samples. One of ordinary skill in the art will recognize that the order in which the compounds are added together is not critical. In addition, unbound TCP may be removed by washing at any point in the assay. The removal of this unbound TCP does not affect potentiation. The desired goal of the assay is to uncover compounds that modulate the TCP-induced binding sites of BFI. Unbound molecules are washed free and the eluent inspected for the presence of [$^3$H]BFI or the test compound. The eluent can easily be scored for the label. The absence of the label indicates the formation of the [$^3$H]BFI/I$_2$ receptor complex. This indicates that the test compound has not effectively competed with [$^3$H]BFI in the formation of the [$^3$H]BFI/I$_2$ receptor complex. The presence of the label indicates that the test compound has competed with [$^3$H]BFI in the formation of the [$^3$H]BFI/I$_2$ receptor complex. In the alternative, the assay can also be performed such that the practitioner measures the label remaining with the protein by means available in the art, more particularly, by filtering the protein and measuring the filter for the presence of the label.

The present invention also provides a process for screening for potential TCP-like compounds that interact with the TCP binding site of the protein but which either do not inhibit MAO or inhibit MAO to a lesser degree than TCP. The process comprises the steps of:

a) preparing tissue preps selected from human brain, kidney or platelets;

b) introducing [$^3$H]BFI to the human tissue preps in the presence and absence of TCP;

c) exposing the tissue preps which contains [$^3$H]BFI only to a potential TCP-like test compound;

d) removing non-specifically bound TCP, test compound or free [$^3$H]BFI;

e) comparing the concentration of [$^3$H] BFI bound to the tissue preps containing the test compound with the concentration of [$^3$H]BFI in the tissue prep in which TCP was added; and f) testing each tissue prep for MAO activity.

The screening system described above provides a sensitive and rapid means to determine compounds which mimic TCP with less MAO inhibition. This screening system may also be adapted to automated procedures such as a PANDEX® (Baxter-Dade Diagnostics) system allowing for efficient high-volume screening of potential therapeutic agents.

In such a screening protocol the receptor is prepared as described in the Examples below. In an alternative embodiment, the receptors may be prepared using recombinant DNA technology techniques.

The receptor may be free in solution or bound to a membrane. Whether the receptor is bound to a membrane or is free in solution, it is generally important that the conformation of the protein be conserved. In a preferred practice of the invention, therefore, the receptor is suspended in a hydrophilic environment employing natural or synthetic detergents, membrane suspensions, and the like.

A sample of a test compound is introduced into the reaction vessel containing the membrane protein (which is obtained from any human source) and [$^3$H]BFI. Alternatively, [$^3$H]BFI may be added prior to or after the introduction of the test compound. A control sample is established which contains the receptor, TCP and [$^3$H]BFI. One of ordinary skill in the art will recognize that the order in which the compounds are added together is not critical. In the absence of TCP, the desired goal of the assay would be to uncover compounds which mimic the action of TCP in enhancing the binding of ligand. Furthermore, such compounds would be evaluated for their ability to interact with MAO so as to develop compounds with superior selectivity. Unbound molecules are washed free and the eluent inspected for the presence of [$^3$H]BFI. The eluent can be scored for the label. Whether the test compound reacts in the same manner as TCP is determined by comparing the amount of [$^3$H]BFI label in the eluent of the sample containing the test compound with the amount of [$^3$H]BFI label in the eluent of the sample containing TCP. The comparison is an indication whether the test compound potentiates additional BFI binding sites as seen in the presence of TCP. In the alternative, the assay can also be performed such that the practitioner measures the label remaining with the protein by means available in the art, not in the eluent. Once the degree of BFI binding is determined, each of the tissue preps is screened for MAO activity using techniques known in the art.

This assay allows for the discovery of new compounds which are mechanistically similar to TCP, but without the typical side effects demonstrated by TCP and other MAO inhibitors.

The embodiments noted above use tissue consisting of cells from living donors. Specifically, human platelets are shown to possess not only highly specific binding sites for BFI as in human brain, but also the sites are likewise potentiated in the presence of TCP but not other types of MAO inhibitors. Moreover, the novel TCP-modified binding sites for BFI are also present in peripheral blood cells, specifically platelets. Therefore, monitoring the density of BFI sites and/or TCP modified sites could be used as a marker for the presence or absence of various human pathologies in the living organism, including but not limited to Alzheimer's Disease, depression, aging, eating disorders, vascular disease, Parkinson's Disease, aggression, stroke, cerebral ischemic disorders and diabetes. In addition, this finding opens up the possibility of a method to monitor therapy of such diseases.

Previous workers have demonstrated that the benzodioxane known as idazoxan can identify specific binding sites in animal and human tissue now known as imidazoline type-2 binding sites. Their function in human pathophysiology is unknown but it has been shown that these sites are modified in numerous disease states including but not limited to Alzheimer's Disease, depression, aging, eating disorders, vascular diseases, Parkinson's Disease, and aggression. I$_2$ sites are located on various intracellular and possibly extra cellular membranes with highest density being found in the mitochondria therein associated with the enzyme MAO. However, it is apparent that the I$_2$ binding sites are not necessarily associated with the active enzyme site which is responsible for the degradation of various endogenous substances such as serotonin and norepinephrine. It is currently thought that the imidazoline receptor site may be a target for as yet unidentified endogenous ligands.

Benzofuranyl imidazoline [2-(2-benzofuranyl)-2-imidazoline] was used to identify the I$_2$ receptor. This new ligand has been described to selectively identify the I$_2$ binding site. It's advantage over idazoxan is that it has higher specificity for the $I_2$ site in relation to an unrelated binding site, the $\alpha_2$ receptor. In all respects however, BFI was previously thought to label the same $I_2$ site as idazoxan. It has now been found that TCP potentially and selectively potentiates binding of BFI in human tissues but does not do the same with idazoxan. Furthermore, the potentiation phenomena is not seen with MAO inhibitors of a different class, specifically pargyline and chlorgyline which are propargylamine type irreversible inhibitors. Moreover, the potentiation phenomenon is highly specific to human tissues since the same phenomenon is not seen in guinea pig and rat tissues.

TCP-enhanced BFI binding has surprisingly been found in both brain and peripheral tissue including kidney and blood platelets. Potentiation was not observed with other known inhibitors such as pargyline or chlorgyline. In addition, the findings are species specific in that potentiation was not seen in rat or guinea pig tissues. Because the TCP modulated sites represent a new binding site for potentiation of imidazoline ligands, their modulation may have important relevance for certain pathophyiological states related to nervous system disorders but also including various cardiovascular diseases such as vascular endothelial dysfunction.

The binding sites described in this invention, and specifically labelled by BFI and related compounds in the presence of TCP may thus be an important target for the development of a new generation of pharmaceuticals having specific applicability in the treatment of various disorders. Furthermore, since it is not clear what the nature of the endogenous ligand is that reacts with imidazoline sites, the novel binding site labelled by [$^3$H]BFI may represent the whole or part of an endogenous receptor for such an endogenous ligand.

While it appears that TCP is unique among MAO inhibitors in producing potentiation of MAO binding, such activity may also be characteristic of other molecules that are structurally related to this compound. For example, a small potentiation can be noted with the hydrazine type inhibitor, phenelzine. Moreover, the potentiation demonstrated with TCP can be prevented by prior incubation of tissues with MAO inhibitors that are of a different class such as pargyline. Since previous studies have established that the $I_2$ binding site and the active site of MAO are distinct entities, our findings suggest the likelihood that molecules similar to TCP can be found that uncover the novel binding site but do not necessarily inhibit MAO.

In various non-human species, others have shown that MAO inhibitors (including TCP) either had no effect or inhibited [$^3$H]idazoxan binding [C. Carpene, et al., J. Pharmacol. Exp. Ther. 272:681–688 (1995); G. Olmos, et al., Br. J. Pharmacol. 108:597–603 (1993); and A. Renouard, et al., Br. J. Pharmacol. 109:625–631 (1993)]. Similarly, in the current process [$^3$H]idazoxan binding in human brain was unaffected by 100 nM TCP, a concentration that maximally stimulated [$^3$H]BFI binding (see FIG. 4b). Interestingly, under identical experimental conditions used to demonstrate TCP potentiation of [$^3$H]BFI binding in human brain no potentiation was seen in rat cortex (see FIG. 4c). The reason for this apparent species difference requires further investigation, however, it is now known that the amino acid sequences of rat and human MAOs differ [J. C. Shih, Monoamine Oxidase: Basic and Clinical Aspects., H. Yasuhara, S. H. Parvez, K. Oguchi, M. Sandler and T. Nagatsu, 15–21, VSP, Utrecht (1993) and Y. -P. P. HSU, et al., J. Neurochem. 53:12–18 (1989)]. Thus, it appears that the [$^3$H]BFI binding potentiation described is most pronounced with the combination of [$^3$H]BFI as radioligand, TCP as the MAO inhibitor and human brain as the binding site. These data suggest that at least in human tissues, it cannot be assumed that [$^3$H]idazoxan and [$^3$H]BFI interact with identical binding site(s). Further, since $I_2$ binding sites and MAO activity are so closely linked physically [F. Tesson, I. Limon-Boulez, P. Urban, M. Puype, L. Vandekerckhove, I. Coupry, D. Pompon, and A. Parini, J. Biol. Chem. 270 9856–9861 (1995)], the recent finding that BFI but not idazoxan inhibits rat liver MAO A and B [C. Carpene, P. Collon, A. Remaury, A. Cordi, A. Hudson, D. Nutt, and M. LaFontan, J. Pharmacol. Exp. Ther. 272 681–688 (1995)] further supports the notion that these compounds have differential binding domains.

Figure 5:
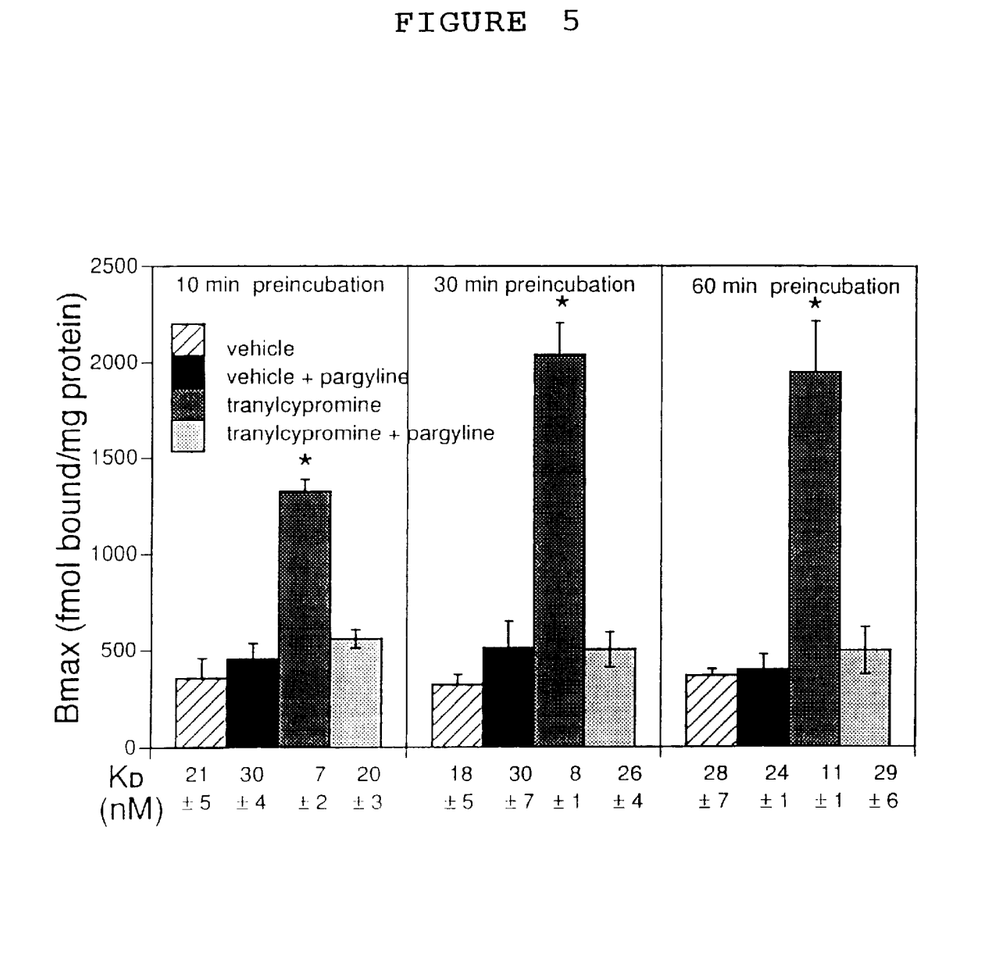
FIG. 5 depicts the effect of pargyline on TCP potentiation of [$^3$H]BFI binding in human brain.

The mechanism by which TCP potentiates binding is unknown, but it appears that endogenous MAO activity is required since preincubation with pargyline to inhibit MAO (>90%) completely abolished the potentiation (see FIG. 5). Also, there appears to be a close inverse relation between inhibition of MAO by TCP and potentiation of [$^3$H]BFI binding (see FIG. 6). At maximal potentiation of [$^3$H]BFI binding (1 $\mu$M TCP) MAO activity was inhibited by 80%. At TCP concentrations >3 $\mu$M MAO was maximally inhibited (95%) while potentiation of [$^3$H]BFI binding decreased progressively in a dose-related fashion. Thus, inhibition of MAO activity by TCP appears closely related to the ability of low concentrations of TCP to increase [$^3$H]BFI binding, however MAO inhibition is unlikely to explain the decrease in binding potentiation at higher TCP concentrations where a clear dissociation between MAO inhibition and potentiation of [$^3$H]BFI binding is evident (see FIG. 6).

TCP is unique compared to other MAO inhibitors, in that it possesses a different mechanism of enzyme inhibition [T. P. Singer, Monoamine Oxidase: Structure, Function, and Altered Functions, T. P. Singer, et al., 7–24, Academic Press, New York (1979); P. Ernsberger, et al., Eur. J. Pharmacol. 134:1–13 (1987)], has higher affinity for $\alpha_2$ adrenoceptors [C. Carpene, et al., J. Pharmacol. Exp. Ther. 272:681–688 (1995)] and can potentially block bovine plasma amine oxidase, an enzyme that is insensitive to other MAO inhibitors and does not possess the same FAD cofactor as MAO [I. Limon-Boulez, et al., J. Pharmacol. Exp. Ther. 276:359–364 (1996)]. Whether any of these differences are relevant to the effect of TCP on [$^3$H]BFI binding is only speculative. Regarding the mechanism of enzyme inhibition, the propargylamine (clorgyline, deprenyl, pargyline) and hydrazine (phenelzine) type inhibitors irreversibly bind to the flavin cofactor following oxidation to reactive intermediates at the active site of MAO [T. P. Singer, Monoamine Oxidase: Structure, Function, and Altered Functions, T. P. Singer, et al., 7–24, Academic Press, New York (1979)]. On the other hand, TCP initially reacts non-covalently with an SH group in the substrate site subsequently forming an imine that covalently attaches to this active site [Id.]. It is possible that binding of the cyclopropylamine moiety at the active site and subsequent imine formation subsequently causes a conformational (allosteric) change in MAO or a closely associated protein and thereby exposes previously cryptic [$^3$H]PFI (but not [$^3$H]idazoxan) binding sites. At higher TCP concentrations, these additional sites may be irreversibly bound by TCP during preincubation thereby decreasing subsequent [$^3$H]BFI binding thus explaining the biphasic potentiation seen (see FIGS. 3 and 6).

Wikberg has previously proposed interacting or interconverting forms of the $I_2$ receptor from analysis of biphasic or shallow competition curves for [$^3$H]idazoxan binding in guinea pig kidney [J. E. S. Wikberg, et al., Pharmacol. Toxicol. 70:208–219 (1991)]. Biphasic binding for clorgyline and clonidine in addition to the dramatic increase in $B_{max}$ and small increase in affinity of [$^3$H]BFI for human brain in the presence of TCP has also been found (see FIG. 5). While it is not clear whether the increase of [$^3$H]BFI binding by TCP represents an increase in new binding sites or exposes previously inaccessible sites by an allosteric mechanism, the large increase in $B_{max}$ and small increase in affinity suggests that the phenomenon is more than a simple allosteric alteration in affinity.

A persistent discrepancy noted in ascribing $I_2$ binding directly to MAO has been the lack of stochiometry between MAO activity and $I_2$ binding. The density of $I_2$ sites is less than the number of MAO molecules both in rat and human tissues and following heterologous expression of MAO in yeast [F. Tesson, et al., J. Biol. Chem. 270:9856–9861 (1995) and M. Sastre et al., J. Neurochem. 61:881–889 (1993)]. Also, a discrepancy in MAO activity and imidazoline binding has been seen using the $I_2$ ligand [$^{125}$I]AZIPI such that photolabeling could be demonstrated in liver membranes but not in platelets despite equivalent amounts of MAO B activity [R. Raddatz, et al., J. Biol. Chem. 270:27961–27968 (1995)]. Thus, whether the human [$^3$H] BFI site is species specific and whether the binding site and monoamine oxidase are the same protein in all tissues requires further study.

The following examples are included for illustrative purposes only and are not meant to limit the invention in any manner.

EXAMPLES

Membrane Preparation for Human Brain

Frozen sections of human cortex (Brodman's areas 8,9, 10), human medulla [defined as the lateral-ventral gray area extending rostrally and caudally the extent of the inferior olivary nucleus but excluding the pyramids, midline structures and all dorsal nuclei and tracts; the area particularly includes the nucleus reticularis lateralis (NRL)] or rat cortex were homogenized in 50 mM Tris-HCl/5 mM EDTA buffer pH 7.5. Membrane fractions were isolated at 4° C. using differential centrifugation as follows: Homogenates were centrifuged at 500×g to remove nuclei and cell debris followed by 45,000×g to obtain the $P_2$ membrane fraction. The $P_2$ pellet was washed twice with 50 mM Tris-HCl buffer. Between washes the pellet resuspension was incubated for 30 min at 25° C. to allow dissociation of endogenous ligands from their receptors. The final pellet was resuspended in 50 mM Tris-HCl, pH 7.5, and stored at −70° C. until used.

Binding Assays

Radioligand binding assays with [$^3$H]BFI or [$^3$H] idazoxan were performed at 21° C. in 50 mM Tris HCl/5 mM EDTA buffer, pH 7.5. Filters were presoaked for 30–45 min in 0.1% polyethyleneimine to reduce nonspecific binding. After equilibration, incubates were filtered through GF/B filters (Brandel; Gaithersburg, Md.) using a 48-channel Brandel harvester. Filters along with trapped radioactivity were washed 3 times for 3 seconds each with ice cold incubation buffer. Specific binding was determined in the presence of 0.1 mM guanabenz and represented >90% of total binding. In some studies membranes were preincubated with pargyline or TCP for 10–60 min and then centrifuged at 39,000×g and washed one time to remove any unbound MAO inhibitor. MAO activity and [$^3$H]BFI binding were determined in preincubated membranes.

MAO Activity

MAO activity was measured with [$^{14}$C]tyramine as substrate using a modification of the method by Yu [P. H. YU, *Neuromethods, Neurotransmitter Enzymes*, A. A. Boulton, G. B. Baker and P. H. Yu, 235–272, Humana Press, Clifton, N.J. (1986)]. Membranes were incubated with [$^{14}$C] tyramine (0.5 mM) at 21° C., pH 7.4 for 40 min. Enzyme activity was stopped by lowering pH to 1.0 with 2 M HCl. The radiolabeled products of MAO degradation (p-hydroxyphenylacetic acid and p-hydroxymandelic acid) were then extracted into toluene ethyl acetate by vortexing for 15 min and aliquots of the organic phase counted. Extraction was enhanced by the addition of a 1 mg/ml carrier concentration of both products and saturating concentration of NaCl. Blank values were measured in incubates immediately stopped by 2M HCl and represented less than 1% label added (or less than 4% product generated).

Data Analysis

Binding data were calculated as fmol bound ligand/mg protein. Protein was determined by the Lowry method. Binding constants were calculated by nonlinear curve fitting (Lundon Software) and the fit to a one or two site model was tested using two-way ANOVA. Relative MAO activity was calculated as CPM/mg protein/min or moles/mg protein/min.

Materials

[$^3$H]BFI (54–70 Ci/mmol) and [$^3$H]idazoxan (45 Ci/mmol) were obtained from Amersham (Arlington Heights, Ill.). Clorgyline, RX821002, and tranylcypromine were purchased from RBI (Natick, Mass.); clonidine, guanabenz, idazoxan, pargyline and phenelzine from Sigma (St. Louis, Mo.); and 2-BFI from Tocris Cookson (Langford, Bristol UK). Cirazoline was a gift from Synthélabo Recherche (Paris, France).

Specific [$^3$H]BFI Binding in Human Brain

The specific binding of [$^3$H]BFI in human brain cortex and NRL was saturable and reached equilibrium in 10 min. Membrane preparations from cortex or NRL were incubated with increasing concentrations of [$^3$H]BFI for 40 min at room temperature. Bound ligand was separated by filtration through GF/B filters. Binding constants were calculated using non-linear curve fitting. Values are mean±SEM of 3–4 experiments. Non-linear curve analysis suggested a single population of binding sites in both brain areas. Binding constants in cortex were $K_D$=11.9±2.7 nM and $B_{max}$= 471±41 fmol/mg and in NRL were $K_D$=9.3±3.5 nM and $B_{max}$=2085±732 fmol/mg. NRL had over 4× as many [$^3$H] BFI binding sites compared to cortex. The data is depicted in FIG. 1B.

Time Course for Equilibration of [$^3$H]BFI Binding in Human Cortex

Cortical membranes were incubated with 8 nM [$^3$H]BFI and amount bound determined at intervals up to 80 minutes. Values are mean±SEM of 3 experiments. The data is depicted in FIG. 1A.

Figure 2:
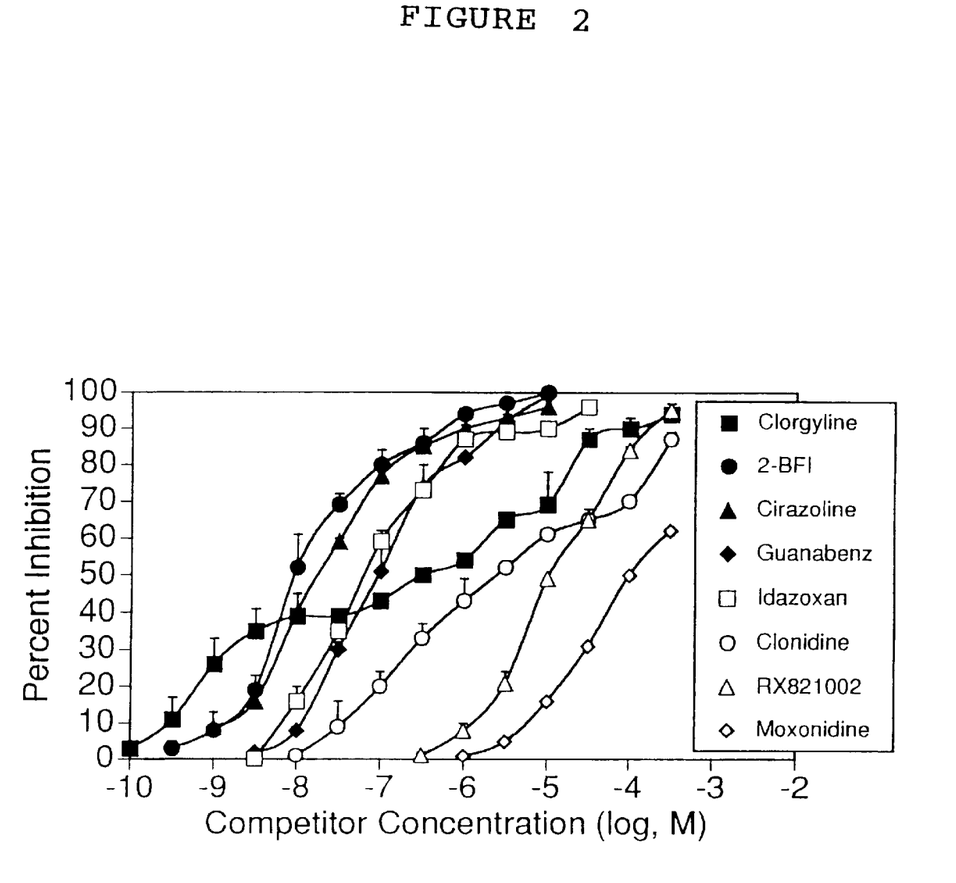
FIG. 2 depicts imidazoline and non-imidazoline ligand competition of [³H]BFI binding in human brain.

Imidazoline and Non-Imidazoline Ligand Competition for [$^3$H]BFI Binding in Human Brain The order of potency for various ligands competing for [$^3$H]BFI binding in human cortex was consistent with the known affinity for $I_2$ binding sites using [$^3$H]idazoxan. Cortical membrane preparations were incubated with 8 nM [$^3$H]BFI for 40 min in the presence of increasing concentrations of competitors. Data represent the percent inhibition of total specific binding and are the mean±SEM of 3 experiments. In order of decreasing potency of inhibition of [³H]BFI binding, clorgyline>BFI>cirazoline>guanabenz idazoxan>clonidine>RX821002. Inhibition constants, ($K_i$), calculated with non-linear curve fitting showed clorgyline and clonidine competition were best fit with a two-site model. $K_i$ values calculated included clorgyline=27.8 nM and 3.7 µM, BFI=9.1±2.1 nM, cirazoline=13.0±4.5 nM, guanabenz=72.5±24.0 nM, Idazoxan=80.4±17.0 nM, clonidine=73.4±24.6 nM and 86.3±11.1 µM, RX821002= 9.4±1.8 µM. The data is depicted in FIG. 2.

Enhancement of [³H]BFI Binding in Human Brain With Tranylcypromine (TCP)

Figure 3A:
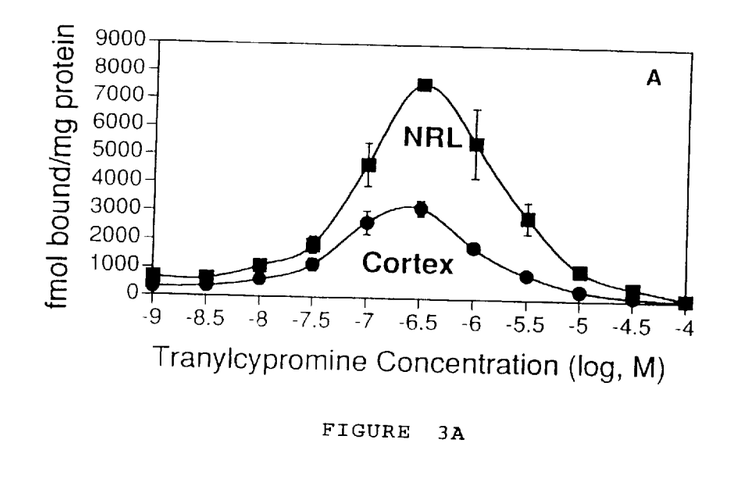
FIGS. 3A, B, and C depict tranylcypromine potentiation of [³H]BFI binding in human brain.
Figure 3B:
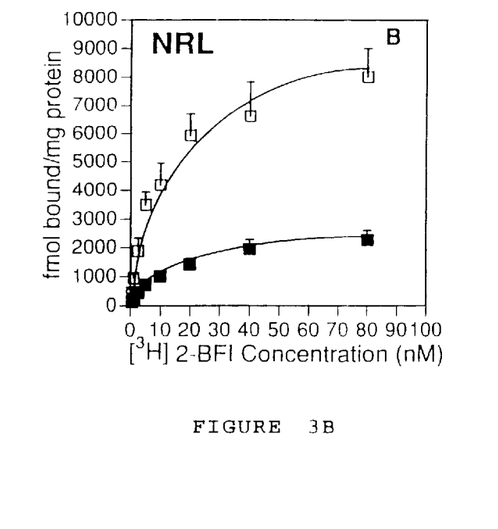
Figure 3C:
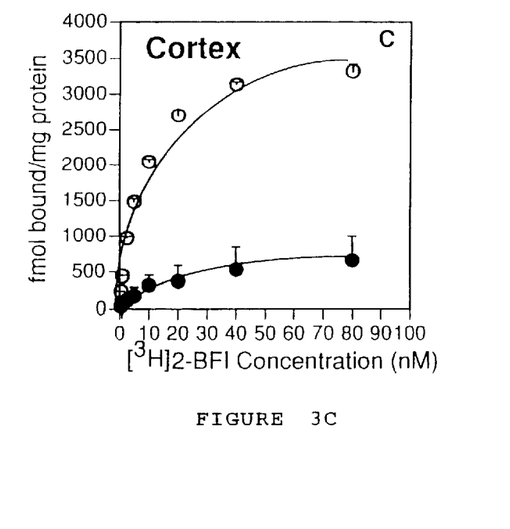

The cyclopropylamine MAO inhibitor, TCP, present during the incubation with [³H]BFI, dramatically enhanced [³H]BFI binding in human NRL and cortex. Membrane preparations from cortex or NRL were incubated with 8 nM [³H]BFI in the presence of increasing concentrations of tranylcypromine. Data are mean±SEM of 3 experiments. [³H]BFI binding was increased in the presence of 10 nM–10 µM TCP with the maximal effect at 0.3 µM (12×control). Concentrations of TCP>10 µM inhibited binding. The data is depicted in FIG. 3A. [³H]BFI binding to human cortex and NRL in the presence of 100 nM TCP was saturable as shown below in FIGS. 3B and C and non-linear curve analysis described a single population of binding sites. Data expressed in fmol/mg are compared in the absence (closed symbols) and presence (open symbols) of 100 nM tranylcypromine. Values are mean±SEM of 3 experiments. In cortex, TCP increased $B_{max}$ to 3494±728 fmol/mg from 471±41 fmol/mg and decreased $K_D$ to 6.0±1.0 nM from 11.9±2.7 nM. In NRL, TCP increased $B_{max}$ to 8393±1273 fmol/mg from 2083±732 fmol/mg with no effect on $K_D$.

Specificity of TCP Effect

Figure 4A:
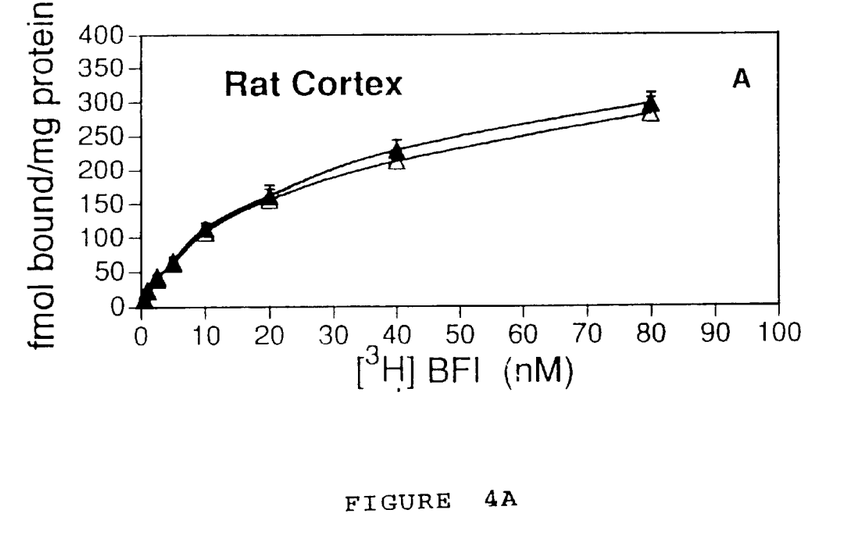
FIG. 4A depicts saturation binding of [$^3$H]BFI in rat cortex with and without TCP.
Figure 4B:
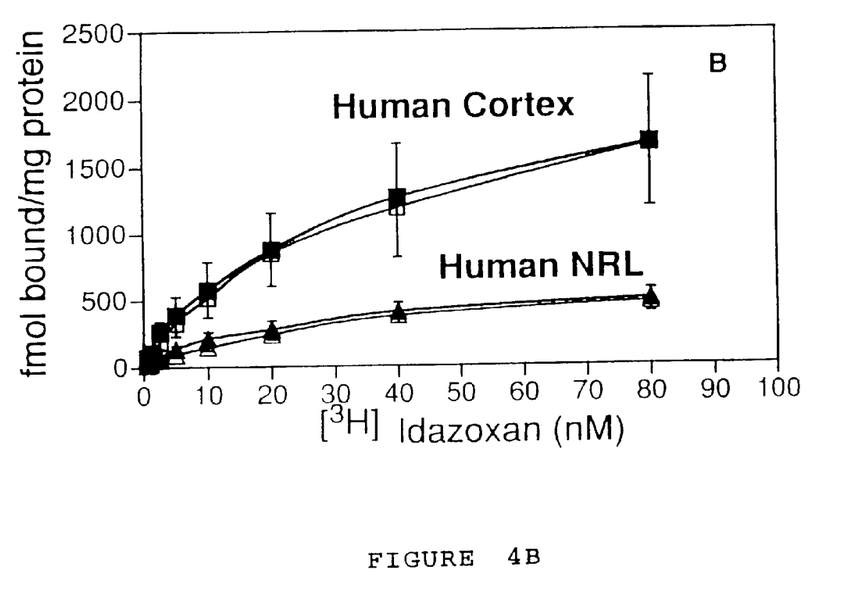
FIG. 4B depicts saturation binding of [$^3$H]idazoxan in human brain with and without TCP and FIG. 4C depicts competition of [$^3$H]BFI binding in human cortex by MAO inhibitors other than TCP.
Figure 4C:
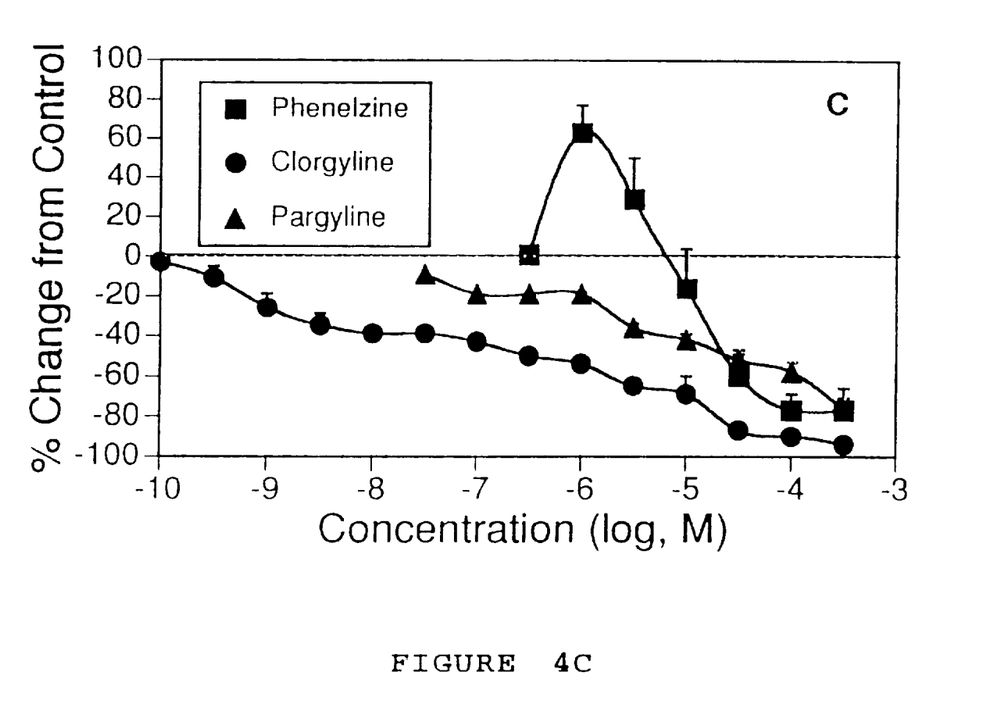

TCP did not enhance [³H]BFI binding in rat cortex. Preparation of rat cortical membranes and incubation conditions were identical to those used for human cortex. Data are mean±SEM of 3 experiments. TCP also did not increase [³H]idazoxan binding in human cortex or NRL. Data are mean±SEM of 3 experiments. Moreover, potentiation of [³H]BFI binding in human cortex was not seen with the MAO inhibitors, pargyline and clorgyline, although a slight increase was noted with phenelzine at 1 µM. Data are mean±SEM of 3 experiments. The data is depicted in FIGS. 4A, 4B and 4C.

Effect of MAO Inhibition on Tranylcypromine-enhanced [³H]BFI Binding

Preincubation with pargyline (10 µM) to inhibit MAO activity abolished the ability of TCP to increase [³H]BFI binding as well as its ability to increase [³H]BFI affinity in human cortex. Cortical membranes were preincubated for 10, 30 or 60 min with 10 µM pargyline, then washed and incubated with 8 nM [³H]BFI in the absence and presence of 100 nM TCP. Data are mean±SEM of 3 experiments. Basal MAO activity was inhibited by 90% at all durations of pargyline preincubation. The 4–7 fold increase in $B_{max}$ and the 3 fold decrease in $K_D$ for [³H]BFI binding in the presence of TCP was prevented with the inhibition of MAO activity. The data is depicted in FIG. 5.

Figure 6:
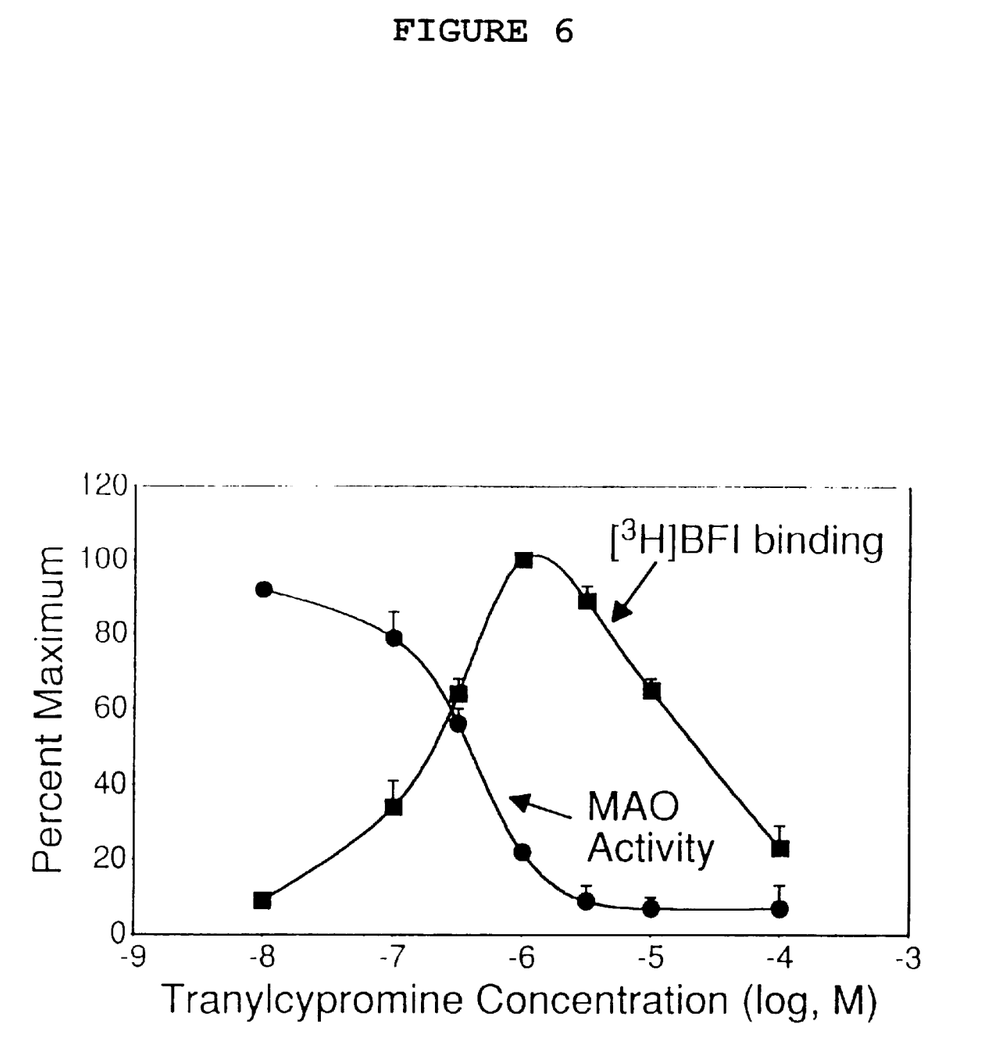
FIG. 6 depicts the effect of preincubation with increasing concentrations of TCP on [$^3$H]BFI binding and MAO activity in human brain.

Effect of Preincubation With Increasing Concentrations of TCP on [³H]BFI Binding and MAO Activity in Human Brain Preincubation with increasing concentrations of TCP for 40 min and subsequent removal of free TCP, resulted in biphasic binding of [³H]BFI similar to experiments in which free TCP was present throughout the incubation. Cortical membranes were preincubated for 40 min with 10 nM–100 µM TCP, then washed and either incubated with 8 nM [³H]BFI to measure binding or 10 µM [³H]tyramine to measure MAO activity. Data are expressed as percent of maximum binding or MAO activity and represent the mean±SEM of 3 experiments. Maximal [³H]BFI binding was 1861±157 fmol/mg and basal MAO activity was 245±51 cpms/min/mg. Binding was potentiated in a dose-related manner from 10 nM–1 µM TCP with a reciprocal inhibition of MAO activity. At concentrations of TCP greater than 1 µM, [³H]BFI binding exhibited a dose-related decrease in potentiation with no further change in MAO activity after maximal inhibition at 3 µM TCP. The data is depicted in FIG. 6.

Membrane Preparation for Human Platelets

Packed human platelets, one day out of date, were obtained from the Central Indiana Regional Blood Center. Six units (approximately 350 ml) were mixed with 3 mg of phenyl methyl sulfonyl fluoride and centrifuged at 1000×g at room temperature (RT) for 12 minutes to remove red blood cells. The supernatant was then centrifuged at 31,000×g for 12 minutes to pellet platelets. Pellets were flash frozen on ethanol/dry ice for 5 minutes, followed by thawing at RT for 10 minutes, resuspending in 22 mM Hepes Na, pH 7.4, and then centrifugation at 31,000×g at 4° C. for 12 minutes. The freeze/thaw cycle was repeated a total of 3 times with the last centrifugation at 48,000×g for 15 minutes. The final pellet was resuspended in 5 mM Hepes Na, pH 7.4, 0.5 mM EGTA, 0.5 mM $MgCl_2$ (HME) with gentle homogenization (glass homogenizer, maximum 10 strokes). Platelet membranes (5 ml) were layered on a 14.5% (15 ml)/34% (15 ml) sucrose gradient and centrifuged at 4° C. for 90 minutes at 105,000×g in a swinging bucket rotor (SW28; XL-80 Beckman ultracentrifuge). Pellets, containing platelet inner membranes, were resuspended in cold distilled water and centrifuged at 120,000×g for 40 minutes. The final pellet was resuspended in HME and stored at −70° C. until used in binding or enzyme activity assays.

Binding With Platelets

Using the above technique with human platelets, 109±40 fmol/mg protein of labelled [³H] BFI was bound to the internal membranes in the absence of TCP. In the presence of 1 mM TCP 3698±356 fmol/mg protein [³H] BFI was bound (about 34 fold potentiation).

Membrane Preparation for Human Kidney Cortex and Kidney Medulla

Membrane preparation for human kidney cortex and kidney medulla were prepared in the same manner as for brain cortex and NRL.

Binding With Human Kidney Tissue $I_2$ binding sites are also known to be present in tissue types in the body, i.e., in the human kidney. Human kidney contained 772±96 fmol/mg protein of [³H] BFI in the absence of TCP whereas in the presence of 1 µM TCP 6741±714 fmol/mg protein, [³H] BFI was bound (about an 8 fold potentation).

What is claimed is:

1. A process for discovering agents that compete with a selective $I_2$ ligand for binding to the TCP-potentiated binding sites, said screening system comprising the steps of:

a) preparing a tissue from human brain, kidney or platelets;

b) exposing said tissue sample to TCP and a test compound;

c) exposing the tissue sample to a selective $I_2$ ligand containing an imidazoline nucleus simultaneously with or following the introduction of the test compound;

d) removing non-specifically bound test compound and said $I_2$ ligand; and e) quantifying the concentration of bound test compound and/or said $I_2$ ligand.

2. A process, as in claim 1 wherein said $I_2$ ligand is selected from the group consisting of BFI, BU224, BU239, Tracizoline, and Benazoline.

3. A process, as in claim 2 wherein said ligand is BFI.

4. A process for screening for compounds that stimulate $I_2$ binding sites which comprises the steps of:

a) preparing a tissue sample selected from the group consisting of human brain, kidney or platelets;

b) introducing [$^3$H]BFI to the human tissue sample in the presence and absence of TCP;

c) exposing said tissue sample which contains [$^3$H]BFI only to a test compound;

d) removing non-specifically bound TCP, test compound or free [$^3$H]BFI;

e) comparing the concentration of [$^3$H]BFI bound to the tissue sample containing the test compound with the concentration of [$^3$H]BFI in the tissue sample in which TCP was added; and f) testing each tissue sample for MAO activity as a measure of the ability of the test compound to stimulate the $I_2$ binding sites.

* * * * *